US008306593B2

(12) United States Patent
Hwang et al.

(10) Patent No.: US 8,306,593 B2
(45) Date of Patent: Nov. 6, 2012

(54) NONINVASIVE APPARATUS AND METHOD FOR MEASURING BLOOD SUGAR CONCENTRATION

(75) Inventors: In Duk Hwang, Suwon-si (KR); Kun Soo Shin, Seongnam-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1358 days.

(21) Appl. No.: 12/000,779

(22) Filed: Dec. 17, 2007

(65) Prior Publication Data

US 2008/0188724 A1    Aug. 7, 2008

(30) Foreign Application Priority Data

Feb. 1, 2007    (KR) .................. 10-2007-0010506

(51) Int. Cl.
  *A61B 5/1455* (2006.01)
(52) U.S. Cl. ................ 600/316; 600/328; 600/335
(58) Field of Classification Search .............. 600/310, 600/316, 322, 331, 334, 335, 340
  See application file for complete search history.

(56) References Cited

U.S. PATENT DOCUMENTS

| | | | |
|---|---|---|---|
| 4,327,739 A | | 5/1982 | Chmiel et al. |
| 4,927,264 A | * | 5/1990 | Shiga et al. ............... 600/322 |
| 5,638,816 A | * | 6/1997 | Kiani-Azarbayjany et al. ............... 600/316 |
| 5,818,048 A | * | 10/1998 | Sodickson et al. .......... 356/405 |
| 6,289,230 B1 | | 9/2001 | Chaiken et al. |
| 6,846,288 B2 | * | 1/2005 | Nagar et al. ............... 600/316 |
| 6,983,178 B2 | * | 1/2006 | Fine et al. ............... 600/335 |
| 2003/0167002 A1 | | 9/2003 | Nagar et al. |
| 2005/0101846 A1 | * | 5/2005 | Fine et al. ............... 600/316 |
| 2007/0043281 A1 | * | 2/2007 | Fine ............... 600/335 |

FOREIGN PATENT DOCUMENTS

| | | |
|---|---|---|
| JP | 2005-118320 | 5/2005 |
| JP | 2005-218684 | 8/2005 |
| KR | 2001-0040703 | 5/2001 |
| KR | 10-2002-0081763 | 10/2002 |
| KR | 10-2003-0075779 | 9/2003 |
| KR | 10-2005-0079610 | 8/2005 |
| KR | 10-2006-0061838 | 6/2006 |

OTHER PUBLICATIONS

Korean Office Action for corresponding Korean Patent Application No. 10-2007-0010506 dated Feb. 27, 2008 (4 pgs).
Korean language Decision to Grant issued Nov. 14, 2008 in corresponding Korean Patent Application No. 10-2007-0010506.

* cited by examiner

*Primary Examiner* — Eric Winakur
*Assistant Examiner* — Chu Chuan (JJ) Liu
(74) *Attorney, Agent, or Firm* — Staas & Halsey LLP

(57) ABSTRACT

An apparatus noninvasively measures blood sugar concentration. The apparatus includes: a tissue modulation unit applying a pressure to a tissue; a hemoglobin (Hb) concentration measurement unit analyzing an amount of absorption of electromagnetic waves on a first portion of the tissue before and after the applying of the pressure by the tissue modulation unit, and measuring Hb concentration of the tissue; and a photoacoustic module unit analyzing photoacoustic signals to measure blood sugar concentration, and correcting the measured blood sugar concentration based on the measured Hb concentration to output a final blood sugar level, the photoacoustic signals being created from the tissue by emitting a pulse laser ray towards a second portion of the tissue before and after the applying of the pressure by the tissue modulation unit.

20 Claims, 7 Drawing Sheets

NONINVASIVE APPARATUS AND METHOD FOR MEASURING BLOOD SUGAR CONCENTRATION

CROSS-REFERENCE TO RELATED APPLICATIONS

This application claims the benefit of Korean Patent Application No. 10-2007-0010506, filed on Feb. 1, 2007, in the Korean Intellectual Property Office, the disclosure of which is incorporated herein by reference.

BACKGROUND

1. Field

The present invention relates to an apparatus for measuring blood sugar concentration, and more particularly, to a noninvasive biosignal measurement apparatus and method which can accurately measure blood sugar concentration by correcting a hemoglobin (Hb) concentration measurement using a tissue modulation technique.

2. Description of the Related Art

As improved lifestyles have enriched our lives, peoples' concerns about their health also have increased. Therefore, research about home medical appliances which enable a user to readily test the user's health status at all times is being conducted, and new products are also being developed. When the user is in a normal health status, body fluids organically circulate and are adjusted, and thus a constant amount of body fluids are maintained. The body fluids include components, such as blood, urine, interstitial fluids, sweat, saliva, and the like. In particular, each component concentration in the body fluids, such as blood, urine, and the like, becomes a very important parameter to inform the user of the health status. Also, it is necessary to measure the concentration of glucose, hemoglobin (Hb), bilirubin, cholesterol, albumin, creatinine, protein, or urea, in the blood. However, when a living body is infected with any disease, a composition or amount of various components in the body fluids may change, so that the user may encounter an emergency situation. For example, a healthy user maintains a blood sugar concentration at about 80 mg/dl (mg per 100 $cm^3$) before meals, and about 120 mg/dl after meals. To maintain the blood sugar concentration at a constant level, the pancreas produces an appropriate amount of insulin before and after meals, that causes the produced insulin to be absorbed in tissues of the liver and the skeletal muscle. However, when the pancreas does not produce sufficient insulin to maintain normal blood sugar concentration due to diseases or other causes, huge amounts of glucoses may exist in the blood, which may cause a cardiac disorder, arteriosclerosis, hypertension, cataract, cyanosis retinae, neural damage, loss of hearing, diminution in acuity of vision, and the like. Also, in a worst case, the user may die. Accordingly, it is very important to measure the change in the body fluids' components before an extreme incident occurs.

A method of measuring the component concentration of body fluids includes an invasive method of directly drawing a portion of a target component from the body, and measuring the concentration of the target component, and a noninvasive method of measuring the concentration of the target component without directly drawing the target component from the body. In this instance, due to some problems caused by the invasive method, a noninvasive technology capable of readily diagnosing a component in blood is being developed. In a conventional method of measuring the blood sugar concentration, a user draws blood, reacts the drawn blood with a diagnostic reagent, and diagnoses the blood using a clinical analyzer or a color change of a test strip reacted to the diagnostic reagent. However, the conventional method may inflict pain upon a diabetic patient since the diabetic has to draw blood every day. Also, the diabetic patient may become infected with another disease due to repeated operations of drawing blood. Also, the conventional method has disadvantages in that an emergency situation may not be readily handled since constant monitoring is impossible. Also, the diabetic patient may feel a huge economical burden since a great deal of strips and diagnostic reagents are used, and thus also results in environmental pollution.

Accordingly, there is a need for a technology which can measure blood sugar concentration without drawing blood and without a strip and a diagnostic agent so that a diabetic patient may control his blood sugar concentration, or a healthy user may examine a medical test.

SUMMARY

In an aspect of the present invention, a method and apparatus noninvasively measure blood sugar concentration without drawing blood from a body, using photoacoustic technology and tissue modulation.

In another aspect of the present invention, a method and an apparatus noninvasively measure blood sugar concentration and measure and correct measured hemoglobin (Hb) concentration to improve accuracy when measuring blood sugar concentration.

According to an aspect of the present invention, an apparatus noninvasively measures blood sugar concentration, the apparatus including: a tissue modulation unit applying a pressure to a tissue; a hemoglobin (Hb) concentration measurement unit analyzing an amount of absorption of electromagnetic waves on a first portion of the tissue before and after the applying of the pressure by the tissue modulation unit, and measuring Hb concentration of the tissue; and a photoacoustic module unit analyzing photoacoustic signals, and measuring blood sugar concentration, and correcting the measured blood sugar concentration based on the measured Hb concentration to measure a final blood sugar level, the photoacoustic signals being created from the tissue by emitting a pulse laser ray towards a second portion of the tissue before and after the applying of the pressure by the tissue modulation unit.

According to another aspect of the present invention, a method noninvasively measures blood sugar concentration, the method including: analyzing an amount of absorption of electromagnetic waves on a first portion of a tissue; emitting a pulse laser ray towards a second portion of the tissue and analyzing a first photoacoustic signal generated from the second portion of the tissue; applying a pressure to a third portion of the tissue; analyzing the amount of absorption of electromagnetic waves on the first portion of the tissue after the applying of the pressure; emitting the pulse laser ray towards the second portion of the tissue after the applying of the pressure, and analyzing a second photoacoustic signal generated from the second portion of the tissue; calculating the Hb concentration using a difference of the amount of absorption of electromagnetic waves on the first portion of the tissue before and after the applying of the pressure; and measuring the blood sugar concentration of the tissue using a difference between the first photoacoustic signal and the second photoacoustic signal, and correcting the measured blood sugar concentration according to the calculated Hb concentration to calculate the corrected blood sugar concentration.

Additional aspects, features, and/or advantages of the invention will be set forth in part in the description which follows and, in part, will be apparent from the description, or may be learned by practice of the invention.

BRIEF DESCRIPTION OF THE DRAWINGS

These and/or other aspects, features, and advantages of the invention will become apparent and more readily appreciated from the following description of embodiments, taken in conjunction with the accompanying drawings of which.

DETAILED DESCRIPTION OF THE EMBODIMENTS

Reference will now be made in detail to embodiments of the present invention, examples of which are illustrated in the accompanying drawings, wherein like reference numerals refer to the like elements throughout. The embodiments are described below to explain the present invention by referring to the figures.

Figure 1:
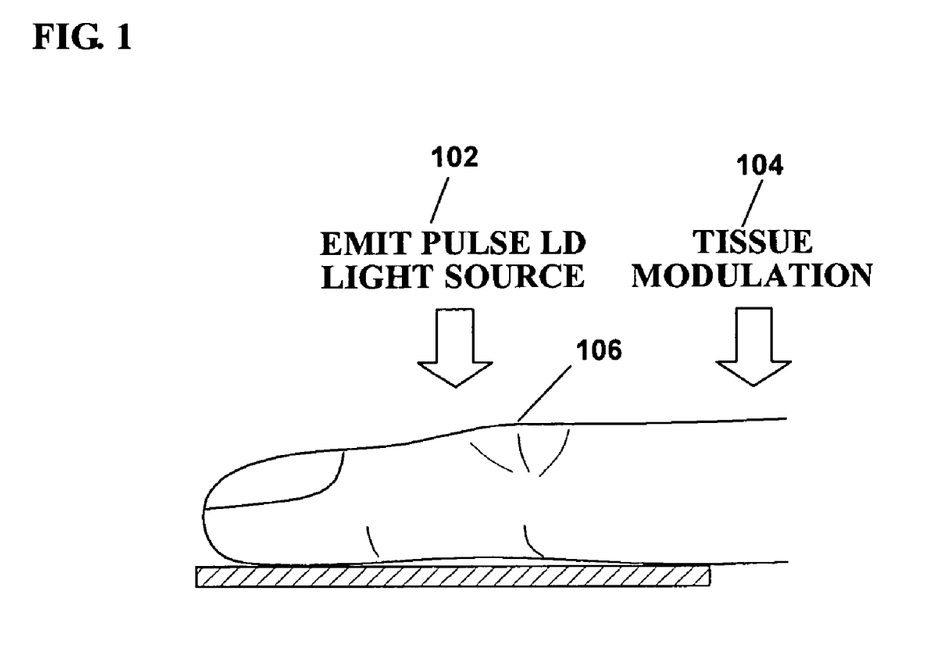
FIG. 1 illustrates an apparatus for noninvasively measuring blood sugar concentration according to an embodiment of the present invention.

FIG. 1 illustrates an apparatus for noninvasively measuring blood sugar concentration according to an embodiment of the present invention.

Referring to FIG. 1, a photoacoustic technology applies a photoacoustic effect to a physical phenomenon corresponding to a basic theory of photoacoustic spectroscopy. In this instance, the photoacoustic effect represents a phenomenon in which an acoustic signal of a frequency identical to a scanned light is created when modulated light is scanned to a medium, such as a tissue, at uniform time intervals. The phenomenon occurs since the medium absorbing photon energy enters an excited state in an aspect of quantum mechanics, and then is relaxed to a ground state. A process of creating a photoacoustic signal may include two schemes. One scheme is a direct photoacoustic generation scheme in which a medium absorbing light is changed into elastic waves to generate a photoacoustic signal. The other scheme is an indirect photoacoustic generation scheme in which a thermal transmission is performed on a coupling material adjacent to a medium absorbing light. In this case, the photoacoustic signal includes information about an optical characteristic, a thermal characteristic, and an elastic characteristic of the medium.

A noninvasive blood sugar concentration measurement apparatus according to the present invention noninvasively measures blood sugar concentration without drawing blood from a body using photoacoustic technology (emit pulse LD light source 102) and tissue modulation 104. The noninvasive blood sugar concentration measurement apparatus emits a pulse laser ray towards an in vivo tissue 106 (hereinafter, "tissue") and then monitors changed amounts of photoacoustic signals generated from the tissue. Also, in the conventional art, due to various variables, such as a tissue cell and changes in a component, blood sugar measurement correction is required for each test subject. However, according to the present invention, blood sugar measurement correction for each test subject is not required by a tissue modulation which variably applies a pressure to the tissue. Specifically, since a photoacoustic signal is analyzed using a difference of an amount of blood in a vein of the test subject, the test subject does not need to draw blood from a body.

Figure 2:
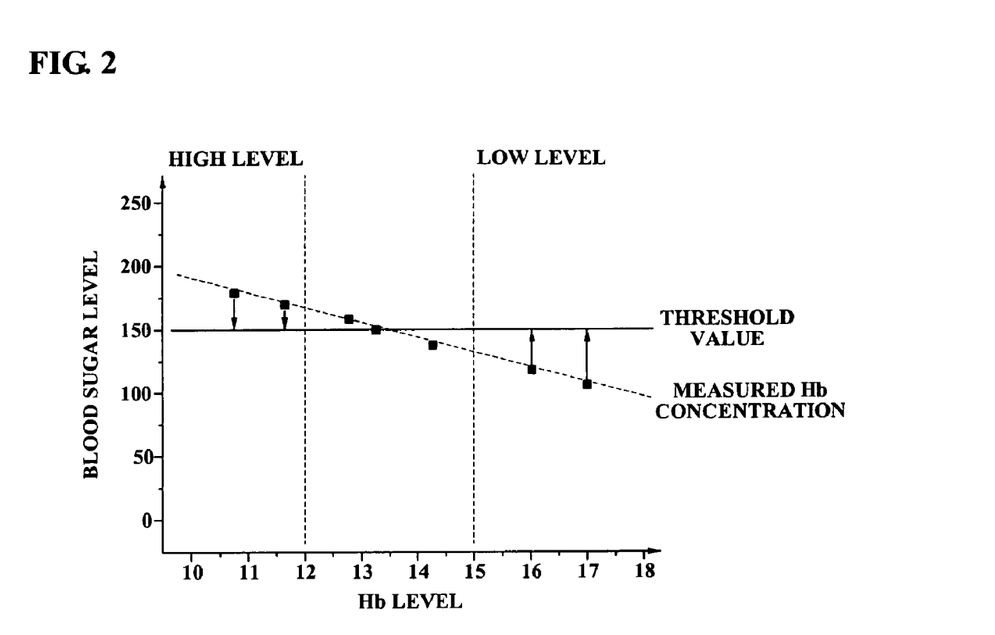
FIG. 2 is a graph illustrating a general relation between an Hb level and a blood sugar level.

FIG. 2 is a graph illustrating a general relation between an Hb level and a blood sugar level.

Figure 3:
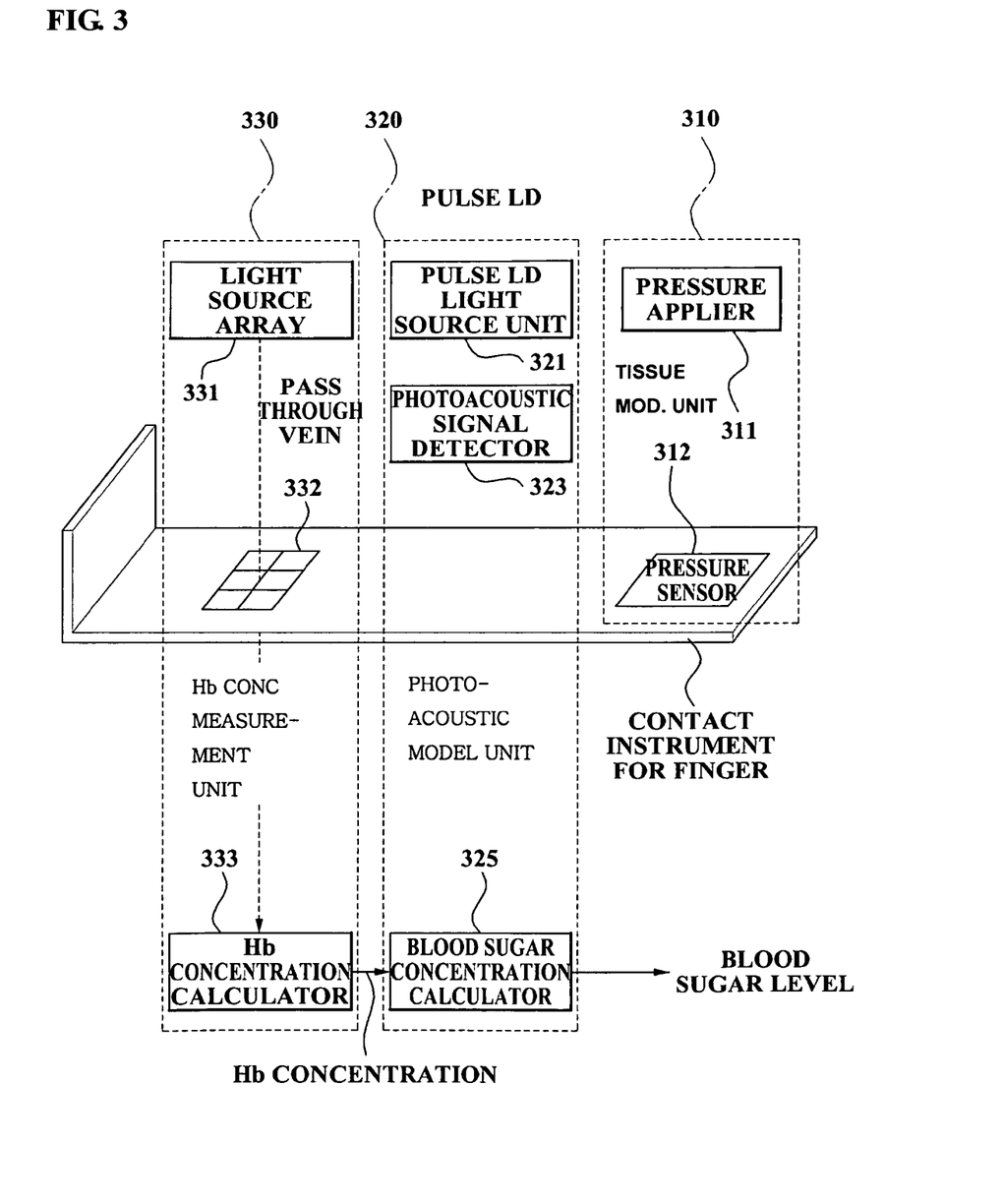
FIG. 3 illustrates configuration elements of an apparatus for noninvasively measuring blood sugar concentration according to an embodiment of the present invention.

In FIG. 2, distribution of an Hb concentration measured in the Hb concentration measurement unit 330 of FIG. 3 is illustrated. The distribution display illustrates that, as the Hb level decreases, the blood sugar level increases. Conversely, as the Hb level increases, the blood sugar level decreases.

Under the circumstance, when a predetermined threshold value, i.e., a normal range of the Hb concentration, corresponds to blood sugar level 150, the blood sugar concentration calculator 325 of a photoacoustic module unit 320 of FIG. 3 decreasingly corrects the measured Hb concentration at a high level, i.e., at a range of less than 12 of FIG. 2, and increasingly corrects the measured Hb concentration at a low level, i.e., at a range of greater than 15 of FIG. 2. Consequently, the distribution of the Hb concentration approaches the threshold value to be paralleled with respect to an entire Hb level.

Accordingly, in the present invention, a blood sugar concentration may be accurately measured since a measured blood sugar concentration is corrected by the Hb concentration, and an influence of the Hb is minimized.

FIG. 3 illustrates configuration elements of an apparatus for noninvasively measuring blood sugar concentration according to an embodiment of the present invention. Referring to FIG. 3, the noninvasive blood sugar concentration measurement apparatus includes a tissue modulation unit 310, a photoacoustic module unit 320, and an Hb concentration measurement unit 330.

The noninvasive blood sugar concentration measurement apparatus noninvasively measures blood sugar concentration in a predetermined portion of a finger or forearm contacting with a predetermined contact instrument. The tissue modulation unit 310 applies a pressure to a tissue. In this instance, the tissue may correspond to the portion of the finger or forearm, and the tissue modulation unit 310 applies a predetermined pressure between the contact instrument for contacting the tissue and a predetermined portion of the tissue.

Also, the tissue modulation unit 310 may include a pressure applier 311 and a pressure sensor 312. The pressure sensor 312 is provided to the contact instrument for contacting the tissue, and senses the pressure applied to the predetermined portion of the tissue. Also, the pressure applier 311 applies the pressure between the contact instrument and the predetermined portion of the tissue by using a result of the sensing which is fed back from the pressure sensor 312.

The Hb concentration measurement unit 330 analyzes an amount of absorption of electromagnetic waves on a first portion of the tissue before and after the applying of the pressure by the tissue modulation unit, and measures Hb concentration of the tissue. Specifically, the Hb concentration measurement unit 330 analyzes the amount of absorption of electromagnetic waves before the applying of the pressure, and also analyzes the amount of absorption of electromagnetic wave after the applying of the pressure to measure the Hb concentration of the tissue.

Particularly, in the embodiment of the specification, the Hb concentration measurement unit 330 may be configured in a reflection type, and measures the Hb concentration of the tissue by analyzing information about how the electromagnetic waves of predetermined waves, irradiated on a specific portion of the tissue before and after the applying of the pressure, are reflected. The configuration of the reflection type is to improve measurement accuracy by eliminating an error caused by light preventing obstacles, such as a bone and a large vein, in a finger penetration type.

Also, the Hb concentration measurement unit 330 may improve accuracy when measuring the Hb concentration by analyzing differences of an amount of absorption, which differences are caused by differences of body fluids in the tissue after applying the pressure on the tissue.

The Hb concentration measurement unit 330 includes a light source array 331, an optical sensor 332, and an Hb concentration calculator 333. The light source array 331 has a plurality of light sources generating the electromagnetic waves. The optical sensor 332 senses the electromagnetic waves when the electromagnetic waves are generated from the plurality of light sources of the light source array 331 and pass through the first portion of the tissue. The optical sensor 332 is installed in the contact instrument for contacting the tissue 106. Also, the Hb concentration calculator 333 calculates the amount of absorption of electromagnetic waves 301 on the first portion, sensed by the optical sensor 332 before and after the applying of the pressure 302 to calculate the Hb concentration.

The photoacoustic module unit 320 corrects the measured blood sugar concentration based on a threshold value of the Hb concentration measured from the Hb concentration measurement unit 330 to calculate the final blood sugar level. For the above operation, the photoacoustic module unit 320 includes a pulse laser diode (LD) light source unit 321, a photoacoustic signal detector 323, and a blood sugar concentration calculator 325. The pulse LD light source unit 321 generates a laser ray having a pulse wavelength, and emits the laser ray towards the second portion of the tissue 106. The photoacoustic signal detector 323 detects a photoacoustic signal generated from the second portion of the tissue after emitting the laser ray. The blood sugar concentration calculator 325 measures blood sugar concentration from the detected photoacoustic signal, and corrects the measured blood sugar concentration according to the Hb concentration measured by the Hb concentration measurement unit 323 to calculate a final blood sugar level. In this instance, the photoacoustic signal detector 323 may include a piezoelectric (PZT) device. The photoacoustic module unit 320 according to an exemplary embodiment of the present invention will be described in detail with reference to FIG. 4.

Figure 4:
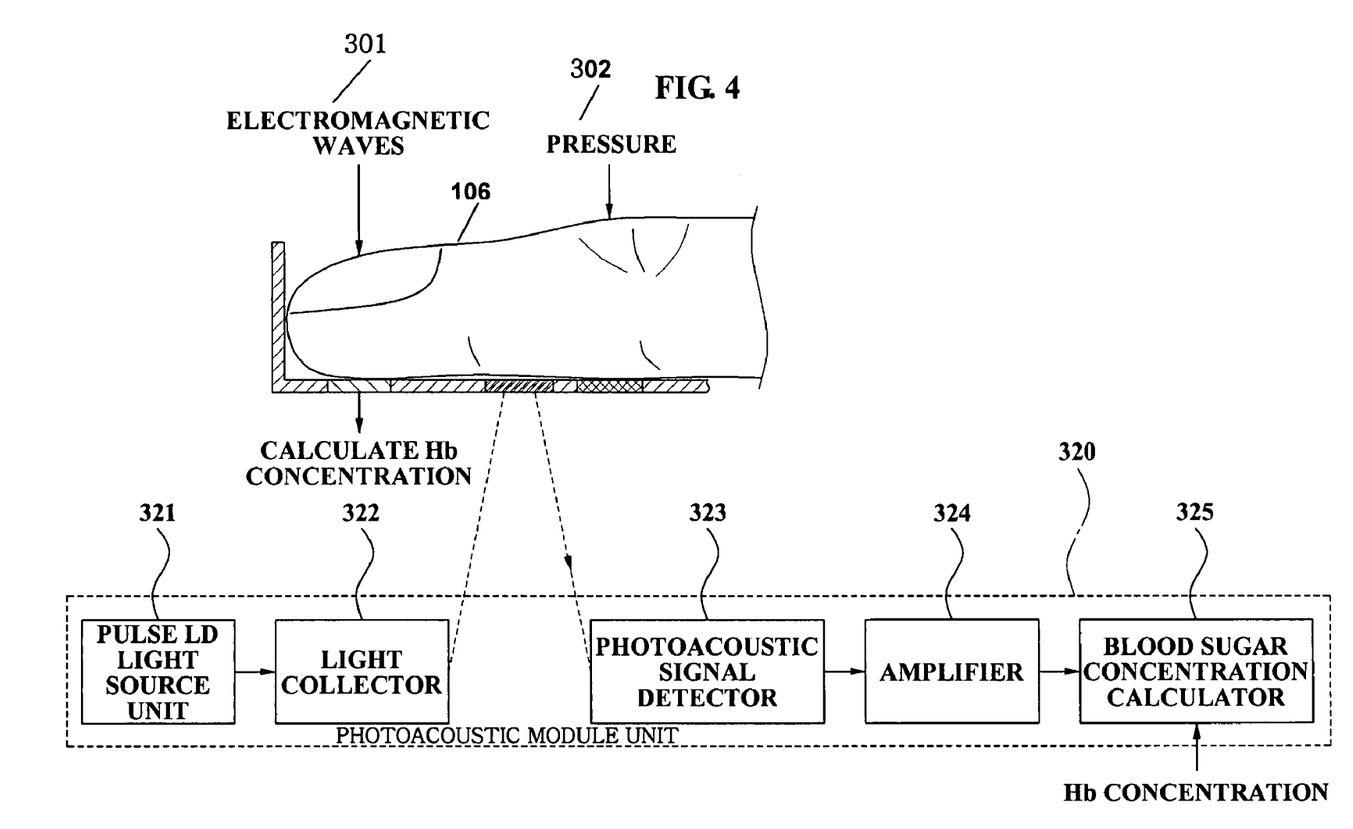
FIG. 4 is a block diagram illustrating configuration elements of a photoacoustic module unit according to an embodiment of the present invention.

FIG. 4 is a block diagram illustrating configuration elements of a photoacoustic module unit 320 according to an embodiment of the present invention.

Referring to FIG. 4, the photoacoustic module unit 320 may further include a light collector 322 and an amplifier 324 in addition to the pulse LD light source unit 321, the photoacoustic signal detector 323, and the blood sugar concentration calculator 325 which have been described above with reference to FIG. 3. The light collector 322 collects the laser ray, generated from the pulse LD light source unit 321, on the second portion of the tissue. The amplifier 324 eliminates noise in the photoacoustic signal detected by the photoacoustic signal detector 323, and amplifies the photoacoustic signal in which the noise is eliminated. A method of noninvasively measuring blood sugar concentration according to an embodiment of the present invention will be described in detail with reference to FIG. 5.

Figure 5:
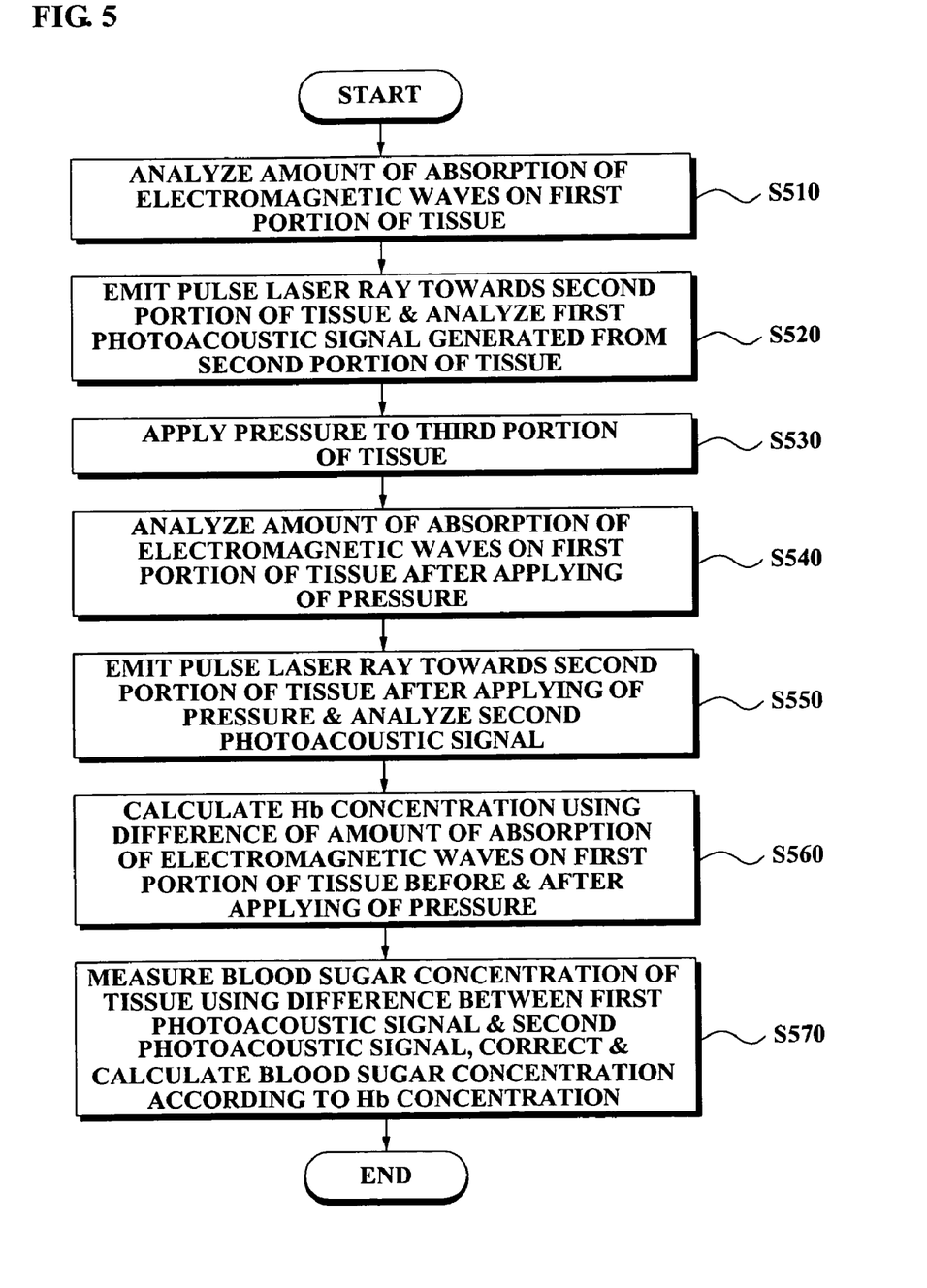
FIG. 5 is a flowchart illustrating a method of noninvasively measuring blood sugar concentration according to an embodiment of the present invention.

FIG. 5 is a flowchart illustrating a method of noninvasively measuring blood sugar concentration according to an embodiment of the present invention.

Referring to FIG. 5, when a noninvasive blood sugar concentration measurement apparatus is turned on, the above-described modulation unit 310, the photoacoustic module unit 320, and the Hb concentration measurement unit 330 start to operate. In operation S510, the Hb concentration measurement unit 330 analyzes an amount of absorption of electromagnetic waves on a first portion of a tissue. In this instance, the light source array 331 may include the plurality of light sources generating the electromagnetic waves. Also, the light source array 331 may generate the electromagnetic waves having a wavelength of less than 1300 nm, for example, near infrared rays, so that an amount of electromagnetic waves absorbed by moisture in blood may be reduced. In this instance, the light source array 331 may generate a plurality of electromagnetic waves having the wavelength of 810 nm and 950 nm respectively. Before the tissue modulation unit 310 applies the pressure, the electromagnetic waves having the wavelength of 810 nm generated from the light source array 331 pass through the tissue and are sensed by the optical sensor 332. As described above with reference to FIG. 4, the optical sensor 332 may be installed in the contact instrument for contacting the finger. The optical sensor 332 generates uniform electrical signals according to the strength of the electromagnetic waves passing through the finger. With respect to the generated electrical signals, the Hb concentration measurement unit 333 measures an amount of absorption of electromagnetic waves in the vein. A value indicating the amount of absorption, which is calculated by the Hb concentration calculator 333 before the applying of the pressure by the tissue modulation unit 310, is stored in a predetermined memory.

In operation S520, the pulse LD light source unit 321 emits a pulse laser ray towards a second portion of the tissue, the light collector 322 collects the pulse laser ray, the photoacoustic signal detector 323 detects a first photoacoustic signal generated from the second portion of the tissue, the amplifier 324 amplifies the detected first photoacoustic signal, and the blood sugar concentration calculator 325 analyzes a blood sugar level from the first photoacoustic signal. In this instance, values calculated by the photoacoustic module unit 320 before the applying of the pressure by the tissue modulation unit 310 may be stored in a predetermined memory.

In operation S530, the tissue modulation unit 310 applies a pressure to a third portion of the tissue. The pressure sensor 312 of the tissue modulation unit 310 may be installed in the contact instrument for contacting the finger as shown in FIG. 3. The pressure sensor 312 senses the pressure applied between the contact instrument and a third portion of the finger by the pressure applier 311. A result of the sensing is fed back from the pressure sensor 312 to the pressure applier 311. The pressure applier 311 applies a predetermined pressure while adjusting the result to not exceed a set value. In this instance, the pressure may be set to a different value depending on various types of conditions, for example, hypotension/hypertension, overweight/normal weight, age, and the like, which will be described in detail with reference to FIGS. 6 and 7.

Figure 6:
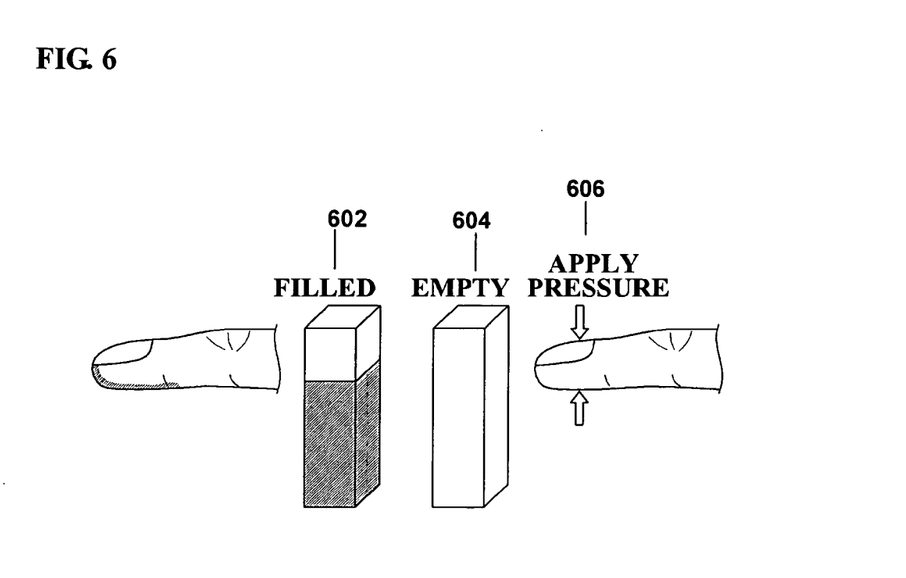
FIG. 6 illustrates a diagram of when blood is expelled from a vein after pressure is applied from a tissue modulation unit.
Figure 7:
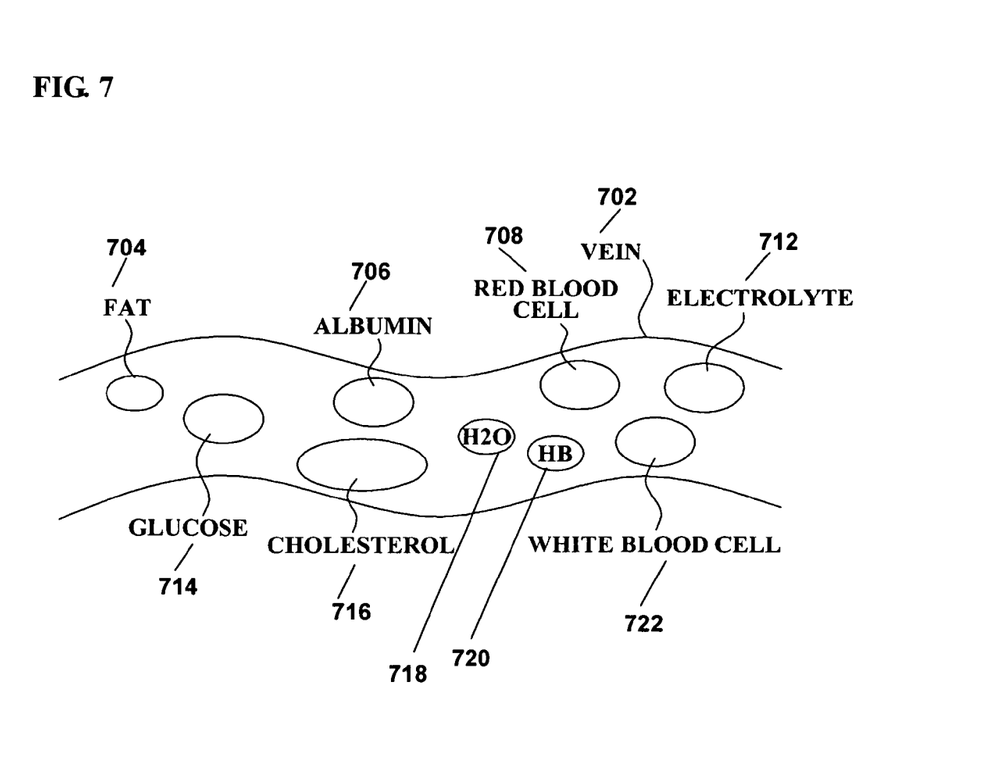
FIG. 7 illustrates components constituting blood in a vein.

FIG. 6 illustrates a diagram of when blood is expelled from a vein after pressure is applied from a tissue modulation unit, and FIG. 7 illustrates components constituting blood in a vein.

Referring to FIGS. 6 and 7, as shown in FIG. 6, an empty container 604 is placed under a contact instrument for contacting a finger before applying the pressure to the finger, and blood fills the container 602 by applying the pressure to the finger. Components such as glucose 714, Hb 720, $H_2O$ 718, a red blood cell 708, a white blood cell 722, fat 704, albumin 706, an electrolyte 712, and cholesterol 706 exist in blood in a vein 702. When the components in blood are applied with the pressure 606 as shown in FIG. 6, the components move to another place where the pressure has no effect, subsequently the portion of the finger that is filled with blood 602 and then is applied with the pressure 606 becomes devoid of blood 604.

Later, the tissue modulation unit 310 applies the pressure to the tissue, for example, the finger, and the photoacoustic module unit 320 and the Hb concentration measurement unit 330 analyze electromagnetic waves and measure the change in the photoacoustic signals in operations S510 and S520. Specifically, in operation S540, the tissue modulation unit 310 analyzes the amount of absorption of electromagnetic waves on the first portion of the tissue after the applying of the pressure. In operation S550, the tissue modulation unit 310 emits the pulse laser ray towards the second portion of the tissue after the applying of the pressure, and analyzes a second photoacoustic signal generated from the second portion of the tissue.

In operation S560, the Hb concentration calculator 333 of the Hb concentration measurement unit 330 calculates Hb concentration of the finger using a difference of the amount of absorption of electromagnetic waves on the first portion of the tissue before and after the tissue modulation 310 applies the pressure to the finger, which will be described with reference to FIG. 8.

Figure 8:
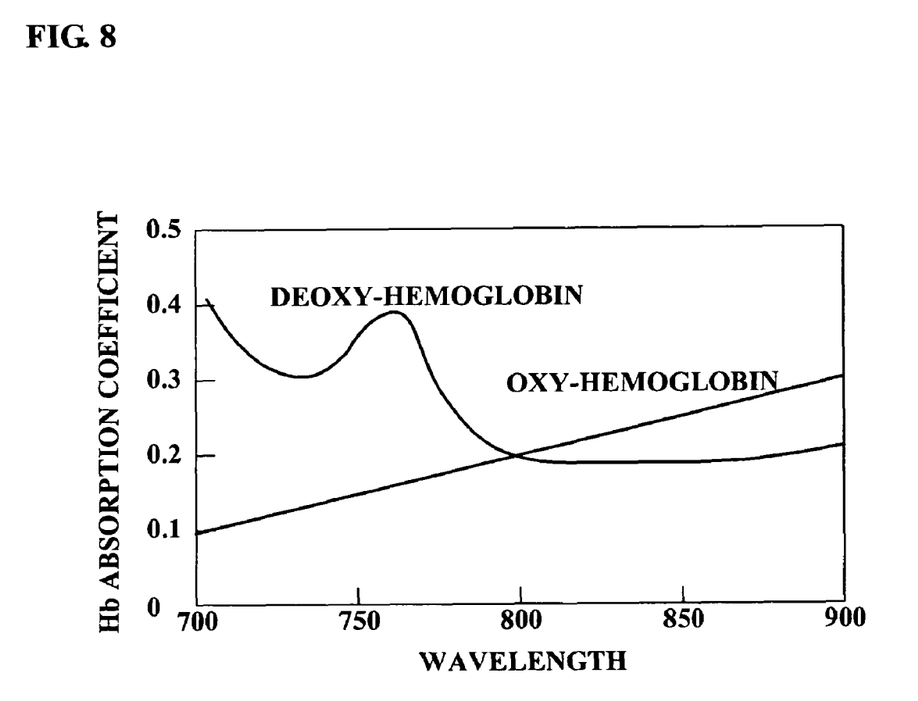
FIG. 8 is a graph illustrating a relation between wavelengths and an Hb absorption coefficient.

FIG. 8 is a graph illustrating a relation between wavelengths and an Hb absorption.

Referring to FIG. 8, an Hb absorption coefficient is different for each wavelength. Electromagnetic waves having a comparatively greater wavelength of the light source array 331 when blood volume is empty after applying of the pressure to the finger by the tissue modulation unit 310 may be used as reference data. Specifically, the Hb concentration of the finger may be calculated using a difference of the amount of absorption of electromagnetic waves generated from the light source array 331 before and after applying of the pressure to the finger by the tissue modulation unit 310. In operation S570, blood sugar concentration of the tissue is measured using a difference between the first photoacoustic signal and the second photoacoustic signal, and the measured blood sugar concentration is corrected according to the calculated Hb concentration, to calculate the corrected blood sugar concentration.

In this instance, the blood sugar concentration may be variously corrected depending on the Hb concentration. As described above with reference to FIG. 2, when a predetermined threshold value is set, and the Hb concentration measured by the Hb concentration measurement unit 330 is greater than the threshold value, the blood sugar concentration may be corrected upwards towards the threshold value according to distributions shown in FIG. 2. Also, when the Hb concentration measured from the Hb concentration measurement unit 330 is less than the threshold value, the blood sugar concentration may be corrected downwards according to distributions shown in FIG. 2.

As described above, when the blood sugar concentration measurement is corrected according to the Hb concentration, the blood sugar concentration may be more accurately calculated.

The invention can also be embodied as computer-readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, optical data storage devices, and carrier waves, such as data transmission through the Internet. The computer readable recording medium can also be distributed over network coupled computer systems so that the computer-readable code is stored and executed in a distributed fashion.

According to the above-described embodiments of the present invention, a method and an apparatus for noninvasively measuring blood sugar concentration without drawing blood from a body utilize photoacoustic technology and tissue modulation.

Also, according to the above-described embodiments of the present invention, a method and an apparatus noninvasively measure blood sugar concentration by measuring and correcting measured hemoglobin (Hb) concentration to improve accuracy when measuring blood sugar concentration.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. An apparatus to measure blood sugar concentration non-invasively, the apparatus comprising:
    a tissue modulation unit adapted to apply a pressure to a tissue;
    a hemoglobin (Hb) concentration measurement unit analyzing an amount of absorption of electromagnetic waves on a first portion of the tissue before and after the applying of the pressure by the tissue modulation unit, and measuring Hb concentration of the tissue; and
    a photoacoustic module unit analyzing photoacoustic signals to measure the blood sugar concentration, correcting the measured blood sugar concentration based on the measured Hb concentration to measure a final blood sugar level, the photoacoustic signals being obtained from the tissue by emitting a pulse laser ray towards a second portion of the tissue before and after the applying of the pressure by the tissue modulation unit.

2. The apparatus of claim 1, wherein the tissue modulation unit is adapted to apply a predetermined pressure between a contact instrument adapted to contact the tissue and a third portion of the tissue.

3. The apparatus of claim 1, wherein the tissue modulation unit comprises:
    a pressure sensor of the contact instrument adapted to contact the tissue, and sense the pressure applied to the third portion of the tissue; and
    a pressure applier adapted to apply the pressure between the contact instrument and the third portion by using a result of the sensing which is fed back from the pressure sensor.

4. The apparatus of claim 1, wherein the tissue corresponds to a portion of a finger or a forearm.

5. The apparatus of claim 1, wherein the Hb concentration measurement unit comprises:
    a light source array having a plurality of light sources generating the electromagnetic waves;

an optical sensor sensing the electromagnetic waves when the electromagnetic waves are generated from the plurality of light sources and pass through the first portion of the tissue; and an Hb concentration calculator calculating an amount of absorption of electromagnetic waves on the first portion sensed by the optical sensor before and after the applying of the pressure, and calculating the Hb concentration.

6. The apparatus of claim 5, wherein the optical sensor is installed in a contact instrument adapted to contact the tissue.

7. The apparatus of claim 1, wherein the pulse laser ray has a wavelength of less than 850 nm.

8. The apparatus of claim 1, wherein the photoacoustic module unit corrects the measured blood sugar concentration based on a threshold value of the Hb concentration to calculate the final blood sugar level.

9. The apparatus of claim 1, wherein the photoacoustic module unit comprises:

a pulse laser diode (LD) light source unit generating a laser ray having a pulse wavelength, and emitting the laser ray towards the second portion of the tissue;

a photoacoustic signal detector detecting a photoacoustic signal generated from the second portion of the tissue after emitting the laser ray; and a blood sugar concentration calculator measuring blood sugar concentration from the detected photoacoustic signal, and correcting the measured blood sugar concentration according to the Hb concentration measured by the Hb concentration measurement unit to calculate a final blood sugar level.

10. The apparatus of claim 9, further comprising:
a light collector collecting the emitted laser ray; and
an amplifier eliminating noise in the photoacoustic signal detected by the photoacoustic signal detector, and amplifying the photoacoustic signal in which the noise is eliminated.

11. The apparatus of claim 9, wherein the photoacoustic signal detector includes a piezoelectric (PZT) device.

12. A method of noninvasively measuring blood sugar concentration, the method comprising:

analyzing an amount of absorption of electromagnetic waves on a first portion of a tissue;

emitting a pulse laser ray towards a second portion of the tissue and analyzing a first photoacoustic signal generated from the second portion of the tissue;

applying a pressure to a third portion of the tissue;

analyzing an amount of absorption of electromagnetic waves on the first portion of the tissue after the applying of the pressure;

emitting the pulse laser ray towards the second portion of the tissue after the applying of the pressure, and analyzing a second photoacoustic signal generated from the second portion of the tissue;

calculating Hb concentration using a difference of the amount of absorption of electromagnetic waves on the first portion of the tissue before and after the applying of the pressure; and measuring blood sugar concentration of the tissue using a difference between the first photoacoustic signal and the second photoacoustic signal, and calculating a corrected measured blood sugar concentration according to the calculated Hb concentration.

13. A non-transitory computer-readable recording medium storing a program to implement a method of noninvasively measuring blood sugar concentration, the method comprising:

analyzing an amount of absorption of electromagnetic waves on a first portion of a tissue;

emitting a pulse laser ray towards a second portion of the tissue and analyzing a first photoacoustic signal generated from the second portion of the tissue;

applying a pressure to a third portion of the tissue;

analyzing an amount of absorption of electromagnetic waves on the first portion of the tissue after the applying of the pressure;

emitting the pulse laser ray towards the second portion of the tissue after the applying of the pressure, and analyzing a second photoacoustic signal generated from the second portion of the tissue;

calculating Hb concentration using a difference of the amount of absorption of electromagnetic waves on the first portion of the tissue before and after the applying of the pressure; and measuring blood sugar concentration of the tissue using a difference between the first photoacoustic signal and the second photoacoustic signal, and calculating a corrected measured blood sugar concentration according to the calculated Hb concentration.

14. A non-transitory computer-readable recording medium storing a program to implement a method of noninvasively measuring blood sugar concentration, the method comprising:

analyzing, upon a pressure being applied to a tissue, an amount of absorption of electromagnetic waves on a first portion of the tissue before and after the applying of the pressure by the tissue modulation unit, and Measuring Hb concentration of the tissue; and determining a final blood sugar level based on measured photoacoustic signals from the tissue, when a pulse laser ray is emitted towards a second portion of the tissue before and after the applying of the pressure, wherein the measured photoacoustic signals are utilized to determine a blood sugar concentration and to correct the measured blood sugar concentration based on the measured Hb concentration.

15. The computer-readable recording medium of claim 14, wherein measuring the Hb concentration of the tissue comprises:

obtaining signals from an optical sensor sensing the electromagnetic waves when the electromagnetic waves are generated from a plurality of light sources and pass through the first portion of the tissue; and calculating an amount of absorption of electromagnetic waves on the first portion sensed by the optical sensor before and after the applying of the pressure, and calculating the Hb concentration.

16. The computer-readable recording medium of claim 14, wherein light absorbed by a receiving medium is changed into elastic waves to generate the photoacoustic signals.

17. The computer-readable recording medium of claim 14, wherein the measured photoacoustic signals include information about an optical characteristic, a thermal characteristic and an elastic characteristic of a receiving medium that absorbs the light.

18. The apparatus of claim 1, wherein light absorbed by the tissue is changed into elastic waves to generate the photoacoustic signals.

19. The apparatus of claim 1, wherein the photoacoustic signals include information about an optical characteristic, a thermal characteristic and an elastic characteristic of the tissue that absorbs the light.

20. The method of claim 12, wherein the photoacoustic signals include information about an optical characteristic, a thermal characteristic and an elastic characteristic of the tissue that absorbs the light.

* * * * *

UNITED STATES PATENT AND TRADEMARK OFFICE
CERTIFICATE OF CORRECTION

PATENT NO. : 8,306,593 B2  
APPLICATION NO. : 12/000779  
DATED : November 6, 2012  
INVENTOR(S) : In Duk Hwang et al.

Page 1 of 1

It is certified that error appears in the above-identified patent and that said Letters Patent is hereby corrected as shown below:

In the Claims:

Column 10, Line 32, In Claim 14, delete "Measuring" and insert -- measuring --, therefor.

Signed and Sealed this  
Seventh Day of May, 2013

Teresa Stanek Rea  
*Acting Director of the United States Patent and Trademark Office*